United States Patent [19]
Thatcher et al.

[11] Patent Number: 5,830,852
[45] Date of Patent: Nov. 3, 1998

[54] COMPOSITIONS FOR INSULIN-RECEPTOR MEDIATED NUCLEIC ACID DELIVERY

[75] Inventors: David R. Thatcher, Cheshire, United Kingdom; Robin E. Offord, Collex-Bossy; Keith Rose, Geneva, both of Switzerland; Hubert F. Gaertner, Archamps, France

[73] Assignee: Cobra Therapeutics, Ltd., London, United Kingdom

[21] Appl. No.: 769,211

[22] Filed: Dec. 18, 1996

Related U.S. Application Data

[60] Provisional application No. 60/008,952, Dec. 20, 1995.

[30] Foreign Application Priority Data

Dec. 19, 1995 [GB] United Kingdom ............... 9525955

[51] Int. Cl.$^6$ .......................... A61K 38/28; C12N 15/00; C12N 15/87
[52] U.S. Cl. .................................. 514/3; 514/4; 514/44; 530/303; 435/172.3
[58] Field of Search ..................... 514/44, 2, 3; 530/350, 530/303; 435/172.3, 320.1

[56] References Cited

U.S. PATENT DOCUMENTS 5,166,320  11/1992  Wu et al. .

FOREIGN PATENT DOCUMENTS

| 0 359 428 A1 | 3/1990 | European Pat. Off. . |
| WO90/02135 | 3/1990 | WIPO . |
| WO 91/17773 | 11/1991 | WIPO . |
| WO 92/19287 | 11/1992 | WIPO . |
| WO96/41813 | 12/1996 | WIPO . |

OTHER PUBLICATIONS

Rose et al., *Peptides 1988* 20:274–276 (1989).
Vilaseca et al., *Bioconjugate Chemistry* 4:515–520 (1993).
Chen et al., 1994, Galactosylated histone–mediated gene transfer and expression, *Human Gene Therapy* 5: 429–435.
Graham and van der Eb, 1973, A new technique for the assay infectivity of human adenovirus 5 DNA, *Virology* 52: 456–467.
Huckett et al., 1990, Evidence for targeted gene transfer by receptor–mediated endocytosis, *Biochem. Pharm.* 40: 253–263.
Kaneda et al., 1987, The improved efficient method for introducing macromolecules into cells using HVJ (Sendai virus) liposomes with gangliosides,*Exp. Cell Res.* 173: 56–69.
Keown, et al., 1990, Methods for introducing DNA into mammalian cells, *Methods Enzymol.* 185: 527–537.
Kucherlapati and Skoultchi, 1984, Introduction of purified genes ito mammalian cells, *Crit. Rev. Biochem.* 16:349–379.
Loyter and Volsky, 1982, Reconstituted Sendai virus envelopes as carriers for the introduction of biological material into cells, *Cell Sur. Rev.* 8:215–266.
Machy et al., 1988, Gene transfer from targeted liposomes to specific lymphoid cells by eletroporation, *Proc. Natl. Acad. Sci. USA* 85:8027–8031.
Midoux et al., 1993, Specific gene transfer mediated by lactosylated poly–L–lysine into hepatoma cells, *Nucleic Acids Res.* 21:871–878.
Rosencranz et al., 1992, Receptor–mediated endocytosis and nuclear transport of a transfecting DNA construct, *Exp. Cell Res.* 199:323–329.
Trubetskoy et al., 1992, Use of N–terminal modified poly(L–lysine)–antibody conjugate as a carrier for targeted gene delivery in mouse lung endothelial cells, *Bioconjugate Chem.* 3: 323–327.
Wigler et al., 1979, Transformation of mammalian cells with genes from procaryotes and eucaryotes, *Cell* 16:777–785.
Wu and Wu, 1987, Receptor–mediated in vitro gene transformation by a soluble DNA carrier system,*J. Biol. Chem.* 262: 4429–4432.
Orkin et al. Report and Recommendations of the panel to assess the NIH investment in research on gene therapy. Distributed by the National Institutes of Health, Bethesda, MD, Dec. 7, 1995.

*Primary Examiner*—Jasemine C. Chambers
*Assistant Examiner*—Deborah J.R. Clark
*Attorney, Agent, or Firm*—Kathleen M. Williams; Banner & Witcoff, Ltd.

[57] ABSTRACT

The invention is based on the discovery of a pharmaceutical preparation for use in gene therapy which includes a therapeutic nucleic acid associated with Insulin-NHCO—$CH_2$—O—N=CH—C-$Lys_{18}$-Cys(S-Pyridyl)-OH in combination with a pharmaceutically acceptable carrier.

5 Claims, No Drawings

COMPOSITIONS FOR INSULIN-RECEPTOR MEDIATED NUCLEIC ACID DELIVERY

FIELD OF THE INVENTION

This application claims the benefit of U.S. Provisional Application No. 60/008,952, filed Dec. 19, 1995, and prior application U.K. 9525955.2, filed Dec. 19, 1995.

The present invention relates to a pharmaceutical composition for delivery of DNA to cells or tissues bearing the insulin receptor.

BACKGROUND OF THE INVENTION

Gene therapy relies on efficient delivery of DNA to target cells, and expression of the delivered DNA in the nucleus of such cells. Different modes of DNA delivery have been proposed, and these involve both viral and non-viral delivery of gene sequences.

Early experiments on introducing DNA into mammalian cells In vitro utilized DNA in precipitated form with low efficiency of transfection and required selectable marker genes (Wigler et al. (1977) Cell 16, 777–85; Graham and Van der Erb (1979) Proc. Natl. Acad. Sci. USA 77, 1373–76 and (1973) Virology 52, 456)). Since this time molecular biologists have developed many other more efficient techniques for introducing DNA into cells, such as electroporation, complexation with asbestos, polybrene, DEAE-Dextran, liposomes, lipopolyamines, polyornithine, particle bombardment and direct microinjection (reviewed by Kucherlapati and Skoultchi (1984) Crit. Rev. Biochem. 16, 349–79; Keown et al. (1990) Methods Enzymol. 185, 527). Many of these methods are unsuitable for use clinically since they give highly variable and relatively poor levels of transfection. Another obstacle to the wider use of existing gene delivery vehicles resides in their instability in vivo. It has been shown that particles of a similar size to the gene delivery vehicles of the prior art are rapidly and efficiently removed from the blood by the reticuloendothelial system (Posse and Kirsch, Bio/Technology 1, 869 (1984)).

Loyter and Volsky (Cell Sur. Rev. 8, 215–266 (1982)) and Kaneda et al. Exp. Cell Res. 173, 56–69 (1987)) describe the reconstitution of viral envelopes as biological carriers including carriers of DNA. In this approach, naturally occurring viruses are isolated, dissolved in detergent containing solvents, the viral nucleic acid removed and the remaining viral components reconstituted in the presence of plasmid DNA. However, this technology has proven to be extremely expensive and difficult to scale up. Moreover, serious safety concerns are connected with the pharmaceutical use of extracted viruses.

Other non-viral gene delivery systems described in the literature merely extend observations on transfection using DNA condensed by synthetic polymers, for example, soluble DNA/polylysine complexes can be generated (Li et al., Biochem. J. 12, 1763 (1973)). Polylysine complexes tagged with asialoglycoprotein have been used to target DNA to hepatocytes in vitro (Wu and Wu, J. Biol. Chem. 262, 4429 (1987); U.S. Pat. No. 5,166,320). Lactosylated polylysine (Midoux et al. (1993) Nuc. Acids Res. 21, 871–878) and galactosylated histones (Chen et al. (1994) Human Gene Therapy 5, 429–435) have been used to target plasmid DNA to cells bearing lectin receptors, and insulin conjugated to polylysine Rosenkrantz et al. (1992) Exp. Cell Res. 199, 323–329) to cells bearing insulin receptors. However, Wagner et al. ( ibid) have shown that the latter approach is even less efficient than standard methods of transfection, and may therefore be considered unsuitable for pharmaceutical development. Monoclonal antibodies have been used to target DNA to particular cell types Machy et al. (1988) Proc. Natl. Acad. Sci. USA 85, 8027–8031; Trubetskoy et al. (1992) Bioconjugate Chem. 3, 323–27 and WO 91/17773 and WO 92/19287).

The insulin receptor has also been used to target gene delivery to cells derived from liver. Huchet et al. (Biochem. Pharmacol. 40, 253 (1990)) obtained low level transfection by using serum albumin derivatized with dimethylaminopropyl groups as a DNA carrier and crosslinked this complex to insulin. Higher transfection activity was obtained by Rosenkrantz et al. (Exp. Cell. Res. 199, 323 (1992)) in which the epsilon-amino group of the C-terminal lysine residue of the insulin beta chain was derivatized with N-succinimidyl 3-(2-pyridyldithio)propionate (SPDP) and coupled to derivatized polylysine.

SUMMARY OF THE INVENTION

The invention is based on a gene delivery vehicle that is capable of targeting cells or tissue types which bear the insulin receptor on their surface, and delivering a gene to that cell or tissue.

The invention encompasses a gene delivery vehicle which includes a nucleic acid binding peptide, $H_2N$-Thr-Lys18-(S-Acetimidomethyl-Cys)-COOH, (SEQ ID NO: 1) linked to insulin or an insulin derivative, and associated with condensed nucleic acid (NA) coding for sequences of therapeutic benefit. The insulin or insulin derivative allows for targeting of the nucleic acid delivery vehicle to mammalian, preferably human, cells or tissue that bear the insulin receptor. The nucleic acid binding peptide thus allows the vehicle to form a complex with condensed nucleic acid and thus to deliver a selected nucleic acid to the insulin receptor-bearing target cell.

The invention also encompasses a pharmaceutical preparation for use in gene therapy, comprising a gene delivery vehicle comprising a therapeutic nucleic acid associated with Insulin-NH—CO—$CH_2$—O—N=$CH_4$—CO-$Lys_{18}$-Cys(S-Pyridyl)-OH in combination with a pharmaceutically acceptable carrier.

The gene delivery vehicle is useful for treating diseases associated with the liver, such as cirrhosis of the liver, hypercholesterolemia, cancer, and infection by hepatitis A, B, C, D or E. Sequences of therapeutic benefit for treatment of such diseases include, for example, ribozymes directed against RNA of infectious organisms or sequences encoding such ribozymes, genes encoding growth factors and growth factor receptors, genes whose products influence progression of the cycle of cell division (e.g., CDK genes and the p53 gene), and the LDL receptor gene.

As used herein, "associated with" or "bound to" refer to noncovalent forms of molecular association, such as charge interactions, hydrogen bonding, and hydrophobic interactions; e.g., positively charged amino groups of the nucleic acid binding component are attracted to negatively charged phosphate groups on the nucleic acid phosphodiester backbone. Alternatively, "associated with" or "bound to" may refer to base pairing; e.g., the hydrophobic and hydrogen bonding interactions found between two strands of DNA.

The nucleic acid binding component of the invention includes an amino acid sequence that is capable of binding to nucleic acid.

The protein hormone insulin or a derivative of insulin acts as the targeting ligand to direct the nucleic acid delivery vehicle to cells expressing the insulin receptor, where the insulin or insulin derivative retains receptor binding properties when conjugated to a nucleic acid binding component. As used herein, "insulin derivative" includes any form of insulin that is capable of specific binding to the insulin receptor and being internalized into the target cell when linked to the nucleic acid delivery vehicle; such as natural or synthetic fragments of the insulin molecule, chemically modified insulin molecules, or chemically modified synthetic or naturally occurring fragments of insulin.

Examples of cells which bear the insulin receptor include but are not limited to hepatocytes, brain cells, adipocytes, lymphoid cells, muscle, epithelial cells, and cancerous tissue, all of which are known to bear a high density of the insulin receptor.

The invention also encompasses methods of ex vivo, in vitro, and in vivo cell-type specific targeting. As used herein, ex vivo targeting refers to targeting of a nucleic acid to an insulin receptor-bearing cell that has been removed from a patient; in vitro targeting refers to targeting of a nucleic acid to an insulin receptor-bearing cell from a cultured cell line; and in vivo cell targeting refers to targeting of an insulin receptor-bearing cell in a mammal such as in a human being.

The invention thus also includes methods of treating an infectious disease, such as is caused by infection by hepatitis virus, particularly hepatitis C, which method includes targeting and incorporating nucleic acids coding for anti-hepatitis C ribozyme genes, into insulin receptor-bearing cells using the above-described delivery vehicle.

The invention thus also encompasses a method of treating a disease of a patient, comprising the steps of: (a) providing a pharmaceutical preparation comprising a gene delivery vehicle comprising a therapeutic nucleic acid associated with Insulin—NH—CO—CH$_2$—O—N=CH—CO-Lys$_{18}$-Cys(S-Pyridyl)-OH in combination with a pharmaceutically acceptable carrier; and (b) administering said pharmaceutical preparation to a patient suffering from a genetic disease.

Ex vivo and in vitro methods will, include the step of contacting the vehicle with an insulin receptor-bearing target cell, whether that cell be in a substantially homogenous population of target cells or in a heterogenous cell population, for a time and under conditions sufficient to allow cell targeting and nucleic acid uptake to occur. One in vivo method includes administering a therapeutically effective amount of the gene delivery vehicle to a mammal, preferably a human. Another in vivo method includes administering a therapeutically effective amount of a homogenous or heterogenous insulin receptor-bearing cell population that has been prepared by contacting the gene delivery vehicle with a target insulin receptor-bearing cell for a time and under conditions sufficient to allow cell targeting and nucleic acid uptake to occur. As used herein, a "therapeutically effective amount" is an amount which confers a therapeutic benefit on a patient.

The invention also encompasses a method of making a delivery vehicle for delivery of a gene to an insulin receptor-bearing cell, comprising the steps of a) oxidizing Thr-Lys18-Cys(S-Pyridyl) peptide (SEQ ID NO: 1), and b) conjugating the oxidized peptide to amino-oxy-acetyl-insulin.

The invention also encompasses a method of making kits for carrying out therapeutic delivery of a gene to a target cell that expresses the insulin receptor, a kit comprising the gene delivery vehicle described herein and packaging materials therefore.

Further features and advantages of the invention will become more fully apparent in the following description of the embodiments and drawings thereof, and from the claims.

DETAILED DESCRIPTION OF THE INVENTION

The invention is based on the discovery of a vehicle for delivery of a gene to insulin receptor-bearing cells, which vehicle includes the ligand insulin or an insulin derivative to target those cells bearing the insulin receptor.

The Structure of Insulin or an Insulin Derivative

The protein hormone insulin, or an insulin derivative, is used to target the nucleic acid delivery vehicle to cells expressing the insulin receptor. Derivatives of insulin include any form of insulin that is capable of binding specifically to the insulin receptor and being internalized into the target cell when linked to the nucleic acid delivery vehicle. The insulin or insulin derivative must recognize and bind with high and specific affinity to the insulin receptor on the target cell type. In practice, the most useful forms of insulin are wild type insulin, or fragments of insulin that are capable of binding to the insulin receptor and being internalized. There are over 500 fragments and derivatives of insulin having biological activity which are known in the art. The invention encompasses those fragments and derivatives of insulin and proinsulin which have at least 10% of the receptor binding affinity of native insulin. The receptor binding affinity of native insulin is determined as taught by Martin et al., 1984, Diabetologia pages 118–120.

Described below is the insulin derivative amino-oxy-acetyl-Insulin.

Structure of the DNA Binding Component

The DNA binding component of the gene delivery vehicle is H$_2$N-Thr-Lys$_{18}$-(S-Acetimidomethyl-Cys)-COOH (SEQ ID NO: 1).

EXAMPLE I

Synthesis of Nucleic Acid Binding Peptide

1. Preparation of H$_2$N-Thr-Lys$_{18}$-(S-Acetimidomethyl-Cys)-COOH

The peptide was synthesized using a Millipore 9050 plus peptide synthesizer in extended synthesis cycle mode (30 mins-1.25 hour couplings increasing during the synthesis). Fmoc-Cys(Acm)-O-PEG-PS-Resin was used. After deprotection of the of the Fmoc group using 20% piperidine in DMF, the subsequent amino acids were coupled in four-fold excess using O-(1H-benzotriazol-1-yl)-tetramethyluronium tetrafluoroborate (TBTU)/1-hydroxybenzotriazole and N,N'-diispropylcarbodiimide as activating agents. When necessary, a four-fold excess of the amino acid, O-(1H-7-aza-benzotriazol-1-yl)-tetramethyluronium hexafluorophosphate and diisopropylethylamine was used to ensure complete coupling to the growing peptide. After the synthesis of the peptide was complete, the N-terminal Fmoc group was removed as described above to give the free amino side chain protected peptide bound to the resin. This was cleaved from the resin using a TFA/water/phenol/thioanisole/1,2-ethanedithiol (82.5:5:5:5:2.5) mixture. Following precipitation with ether and centrifugation, the peptide was purified using gel filtration to give the desired product. When necessary, the Acetimidomethyl (Acm) thiol protecting group may be removed using mercury (II) acetate in 30% acetic acid in water followed by precipitation of the mercury with 2-mercaptoethanol. The resulting free thiol peptide can be purified using gel filtration to give the desired product. The peptide was synthesized using Millipore 9050 plus peptide synthesizer in extended synthesis cycle mode (30 mins-1.25 hour couplings increasing during the synthesis). Fmoc-Cys(Acm)-O-PEGPS-Resin was used. After deprotection of the Fmoc group, using 20% piperidine in DMF, the subsequent amino acids were coupled in four fold excess using O-(1H-benzotriazol-1-yl)-tetramethyluronium tetrafluoroborate (TI3TU)/1-hydroxybenzotriazole and N,N'diisopropylcarbodiimide as activating agents. When necessary, a four-fold excess of the amino acid O-(1H-7-aza-benzotriazol-1-yl)tetramethyluronium hexafluorophosphate and diisopropylethylamine was used to ensure complete coupling to the growing peptide. After the synthesis of the peptide was complete, the N-terminal Fmoc group was removed as described above to give the free amino side chain protected peptide bound to the resin. This peptide was cleaved from the resin using a TFA/water/phenol/thioanisole/1,2-ethanedithiol (82.5:5:5:5:2.5) mixture. Following precipitation with ether and centrifugation, the peptide was purified using gel filtration to give the desired product. When necessary, the acetimidomethyl (Acm) thiol protecting group may be removed using mercury (II) acetate in 30 t acetic acid in water followed by precipitation of the mercury with 2-mercaptoethanol. The resulting free thiol peptide can be purified using gel filtration to give the desired product. The S-pyridyl derivative was obtained by reaction with a 5 fold molar excess of dithiopyridine in 0.1N sodium acetate buffer containing 50% acetonitrile. After 2 h incubation at room temperature the product was purified by reverse phase hplc.

2. Synthesis of Filler Component

A filler component may be added to the assembly reaction during preparation of the gene delivery vehicle. The filler component may be synthesized according to the above-noted procedure for synthesis of the DNA binding component. The filler NBC-II ($H_2$N-NBC-II-(Acetimidomethyl-Cys)-COOH) has the following sequence: $NH_2$ P K K X R X V E K K S P K K A K K P A K S P A - KAKAKAVKPKAAKPKKPKKK RKVEKKSPKKAKKPAAC-COOH (SEQ ID NO: 2).

EXAMPLE II

Functionalization of Insulin

Insulin may be chemically modified according to previously described methods (Offord, R.E. "Semisynthetic Proteins" pp. 235, Wiley, Chichester and New York (1980)), with slight modifications. Briefly, 100 mg Zn-free insulin is dissolved in 1 mL of 1M $NaHCO_3$, diluted with 4 mL dimethylformamide (DMF) and reacted with an equimolar amount of MSC-ONSu (N-Hydroxy succinimide derivative of Methylsulfonyloxycarbonate, Tesser, 1975, in "Peptides", John Wiley, N.Y., pp 53–56) relative to protein amino groups. After 1 h incubation at room temperature, the mixture is acidified and subjected to preparative HPLC on a Waters Prep Nova-Pak $H_2$ $C_{18}$ column (flow rate 20 ml min using a 25–50% B gradient (B gradient is a mixture of 0.1 (w/v) aqueous TFA and acetonitrile:TFA water 900:1:100 (v/w/v) over 50 min. The peak corresponding to all-substituted insulin (as judged by subsequent ESI-MS) is collected and desalted in a double Chromabond (C18 solid phase extraction cartridge (2×1 g of resin in a polypropylene column) Macherey-Nagel, Dornstadt, Germany) equilibrated in 0.1% TFA. The derivative obtained in such reactions is known to be preponderantly the desired N-α, $A^1$-MSC, N-∈-$B^{30}$MSC substituted molecule.

Analysis of the modified protein after overnight incubation in 50 MM DTT allows identification of the B-chain with only a single MSC group (calcd. m/z 3547.8; found m/z, 3549.6±0.4), which is in agreement with the desired structure.

50 mg MSC2-insulin are dissolved in 1 mL N-methylpyrrolidone and reacted with a 10-fold molar excess of Boc-AoA-OSu (Vilaseca et al., Bioconjugate Chem. 4 515–520 (1993)), in the presence of equimolar amounts of HOBt and of sufficient N-ethylmorpholine to bring the pH to approximately 8. After 1 h incubation at room temperature, the reaction medium is acidified and diluted with 0.1% TFA, and the derivatized insulin isolated by semipreparative HPLC on a C8 reverse phase column equilibrated in 0.1% TFA in conjunction with a 35–45B% gradient (described above) over 20 min.

The MSC groups are then cleaved by treatment with sodium hydroxide as described by Offord (loc cit) and the material repurified on the C18 column using 35–45% gradient over 20 mins. The final compound, BOC-AoA-insulin, may be characterized by ESI-MS (calcd. m/z 5950.6; found m/z 5948.1±0.1) and is deprotected by TFA treatment (30 minutes at room temperature) just before conjugation to a polylysine peptide.

EXAMPLE III

Oxidation of the Thr-$Lys_{18}$-Cys(S-Pyridyl) Peptide (SEQ ID NO: 1) and Conjugation to Amino-oxy-acetyl (AOA)-Insulin The Cys-protected peptide (10 mg/ml) is dissolved in 50 mM imidazole, pH 6.9, and 0.2M methionine in water is added as a anti-oxidant scavenger to a 10-fold molar excess over peptide. 50 mM sodium periodate is added to a five-fold molar excess over peptide, and the solution allowed to stand in the dark for 5 minutes at 220° C. The mixture is purified by semipreparative HPLC on a C8 reverse phase column using 0.1% aqueous TFA and a 10% to 60% gradient of 0.1% aqueous TFA in 90% acetonitrile over 25 min.

The isolated oxidized peptide is dissolved into a solution of 5 mg of the AoA-insulin derivative (approximately 2-fold molar excess of peptide over insulin) made up in 0.5 mL 0.1M sodium acetate buffer to which had been added 50 μL acetonitrile, followed by adjustment to pH 3.8 with glacial acetic acid. After 15 h incubation at room temperature, the conjugate is isolated and characterized by ESI-MS (calcd. m/z 8426.1, found m/z 8429.3±0.5). 4 mg of material were isolated by semipreparative HPLC with a 30–45% gradient from the bulk of the reaction mixture. The peak fraction was dried in a speedvac (yield is approximately 4 mg of conjugate).

EXAMPLE IV

During gene transfer a fusogenic peptide may be included in the transfection mix in order to enhance efficiency of transfer of the therapeutic gene. A fusogenic peptide FP useful according to the invention includes the follow sequence: $NH_2$-GLFEAIAGFIENGWEGMIDGGGC(Acm)-COOH (SEQ ID NO: 3), and is synthesized as follows.

1. Synthesis of $H_2$N-FP-(S-acetimidomethyl-Cys)-COOH:

The FP peptide is synthesized using a Millipore 9050 plus peptide synthesizer in extended synthesis cycle mode (1 hour couplings). Fmoc-Cys(Acm)-O-PEG-PS-was used. After deprotection of the Fmoc group using 20% piperidine in DMF, the subsequent amino acids were coupled in four-fold excess using 0-(1H-benzotriazol-1-yl)-tetramethyluronium tetrafluoroborate (TBTU)/1- hydroxybenzotriazole and N,N'-diisopropylcarbodiimide as activating agents. When necessary, a four fold excess of the amino acid, O(1H-7-aza-benzotriazol-1-yl)-tetramethlyroniumhexafluorophosphate and diisopropylethylamine was used to ensure coupling to the growing peptide. After the synthesis of the peptide was complete, the N-terminal Fmoc group was removed as described above to give the free amino side chain-protected peptide bound to the resin. This was cleaved from the resin using a TFA/water/phenol/thioanisole/1,2-ethanedithiol (82.5:5:5:5:2.5) mixture. Following precipitation with ether and centrifugation, the peptide can be purified using gel filtration to give the desired product.

The acetamidomethyl (Acm) thiol protecting group on the peptide may be removed using mercury (II) acetate with water/acetonitrile tl: 0.1 t TFA) as solvent followed by precipitation of the mercury with 2-mercaptoethanol. The resulting free thiol peptide can be purified using gel filtration to give the desired product.

EXAMPLE V

Synthesis of Transfection Complexes

DNA is made up to 20 mg/ml in a transfection buffer (0.15M to 1.0 NaCl; 25 mM HEPES, pH 7.4) The conjugate and peptide is made to an equal volume to the DNA in safe buffer. The DNA is shaken or vortexed while the condensing agent is added at the rate of 0.1 volume per minute. The complex is left at room temperature for at least 30 minutes prior to adding to cells, and can be stored at 4° C. if necessary. Transfection complexes consist of plasmid DNA containing the therapeutic gene or reporter gene, insulin conjugated to $NH_2$-Thr-Lys$_{18}$-Cys-COOH (SEQ ID NO: 4) and unconjugated NBC-II. The transfection complex is synthesised by incubating the three components together, for 30 minutes to 24 hours at room temperature. The prepared complex is centrifuged to remove any aggregated material and then assayed for gene transfer.

Gel Retardation Assay for DNA Condensation

Conjugates or peptides are assayed for their ability to condense DNA using the following method:

The DNA is made up to 20 mg/ml in 150 mM NaCl; 25 mM HEPES, pH 7.4, or in 0.6M NaCl; mM HEPES, pH 7.4 and aliquoted between wells on a multiwell plate. The amount of conjugate or peptide required to give (positive charge:phosphate) ratios of between 0.1 and 5.0 is calculated. This amount is made up to an equal volume to the DNA aliquots (0.05–0.5 ml) in either 150 mM sodium chloride; 25 mM HEPES, pH 7.4 or 0.6M sodium chloride; 25 mM HEPES, pH 7.4. The plate containing the DNA is placed on a plate shaker and shaken while the conjugate or peptide is added at a rate of 0.1 volume per minute. After addition of the condensing agent is complete, the solution is incubated at room temperature for at least 30 minutes. A sample for each (positive charge: phosphate) ratio is analyzed by electrophoresis on an agarose gel. The gel is stained with ethidium bromide and visualized under UV light. Condensed DNA remains in the well of the gel and does not migrate in the electric field.

EXAMPLE VI

Assay for Gene Transfer

The transfection complexes may be assayed for their ability to transfer genes into hepatocytes (HepG2 cells) expressing the insulin receptor. For studies aimed at determining transfection efficiency, the plasmid DNA contains a marker gene for firefly luciferase. For pharmaceutical applications, the plasmid contains a gene whose expression will have a beneficial effect. The transfection complex is incubated with blood cells and the mixture is subjected to electroporation. After incubation, the cells are lysed and assayed for gene expression. In the case of the luciferase reporter gene, luciferin and ATP are added to lysed cells and the light emitted is measured with a luminometer.

Cells are harvested on the day of assay by centrifugation at 1200 rpm for 5 min at room temperature. The cell pellet is resuspended in phosphate buffered saline (PBS) and re-centrifuged. This operation is performed twice. The cell pellet is then suspended in RPMI 1640 (Gibco Ltd.) to make up a suspension of approximately $2.7\times10^6$ cells per ml. The cells are then aliquoted into tubes and 0.75 ml of RPMI medium added, followed by 0.04–0.08 ml of 100 $\mu$m Chloroquine (CQ) or FP peptide and finally 0.25 ml of DNA-complex solution. The transfection is then allowed to proceed by incubating the cells at 37° C. for 4 h. After this time, the cells are harvested by centrifugation at 2000 rpm, suspended in 1 ml of RPMI and re-centrifuged. Finally, the cells are in 0.5 ml RPMI containing 10% fetal bovine serum. At this stage, if necessary, the cells are electroporated at 300 V and 250 $\mu$F using conventional electroporation.

Each 0.5 ml of transfected cell suspension is transferred to a well of a 12 well plastic culture plate containing 1.5 ml of RPMI 10% FBS. The original transfection tube is rinsed with a further 1 ml of medium and the wash transferred to the culture dish making a final volume of 3 ml. The culture plate is then incubated at 37° C. for 24–72 h in an atmosphere of 5% $CO_2$. The contents of each well in the culture dish are transferred to centrifuge tubes and the cells collected by centrifugation at 13,000 rpm. The pellet is resuspended in 0.12 ml of Lysis Buffer (100 mM sodium phosphate, pH 7.8, 8 mM $MgCl_2$, 1 mM EDTA, 1% Triton X-100 and 15% glycerol) and agitated with a pipette. The lysate is centrifuged at 13,000 rpm for 1 minute and the supernatant collected. 80 pl of the supernatant are transferred to a luminometer tube. The luciferase activity is then assayed using a Berthold Lumat L9501 luminometer. The assay buffer used is Lysis buffer containing 10 mM Luciferin and 100 mM ATP. Light produced by the luciferase is integrated over 4 sec and is described as relative light units (RLU). The data are converted to RLU/ml of lysate, RLU/cell or RLU/mg protein (protein concentration of the lysate having been determined in this case by the BioRAD Lowry assay).

The transfection efficiency resulted in the delivery such that 200,000–500,000 relative luciferase units per mg of protein were expressed in the transfected cells.

EXAMPLE VII

Dosage and Pharmaceutical Formulation

The delivery vehicle and plasmid DNA may be formulated separately for parenteral administration or formulated together as the transfection complex. In the latter case the transfection complex may be assembled just prior to use. In the case of a pharmaceutical composition, the plasmid DNA includes a gene whose expression would have some beneficial therapeutic effect on the cells of the recipient.

The delivery vehicle and DNA are exchanged into isotonic phosphate free buffer and sterile filtered through a 0.45 or 0.22 $\mu$ filter. The formulated solution or transfection complex (a mixture of the delivery vehicle, DNA and free DNA condensing component) may be sterile filled and aliquotted into suitable vials. The vials may be stored at 4° C., 20° C. or 80° C. or alternatively the DNA, delivery vehicle or transfection complex may be freeze dried from a buffer containing an appropriated carrier and bulking agent. In these cases, the dosage form is reconstituted with a sterile solution before administration.

Use of this type of pharmaceutical composition in vivo or ex vivo with nucleic acid containing a gene of physiological importance, such as replacement of a defective gene or an additional potentially beneficial gene function, is expected to confer long term genetic modification of the cells and be effective in the treatment of disease. A delivery vehicle of the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" will be determined by the level of enhancement of function of the transferred genetic material balanced against any risk of deleterious side effects. Monitoring levels of gene introduction, gene expression will assist in selecting and adjusting the dosages administered. Generally, a composition including a delivery vehicle will be administered in a single dose in the range of 10 ng–100 ug/kg body weight, preferably in the range of 100 ng–10 ug/kg body weight, such that at least one copy of the therapeutic gene is delivered to each target cell.

Ex vivo treatment is also contemplated within the present invention. A cell population comprising insulin receptor-bearing cells can be removed from the patient or otherwise provided, transduced with a therapeutic gene in accordance with the invention, then reintroduced into the patient.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

We claim:

1. A composition comprising a nucleic acid non-covalently bound to Insulin-NHCO—CH$_2$—O—N=CH—CO-Lys$_{18}$-Cys(S-Pyridyl)-OH in combination with a biologically compatible carrier.

2. A method of preparing a composition comprising
  1. oxidizing Thr-Lys$_{18}$-Cys(S-Pyridyl) peptide (SEQ ID NO: 1), and
  2. conjugating said oxidized peptide to B1 amino-oxyacetyl-insulin.

3. A method of transfecting an isolated insulin receptor-bearing cell with a nucleic acid, comprising the steps of:
  (a) providing a composition comprising a nucleic acid non-covalently bound to Insulin-NHCO—CH$_2$—O—N=CH—CO-Lys$_{18}$-Cys(S-Pyridyl)-OH in combination with a biologically compatible carrier, and
  (b) contacting said insulin receptor-bearing cells with said composition.

4. A method of targeting isolated insulin receptor-bearing cells for delivery of a nucleic acid, comprising the step of contacting said insulin receptor-bearing cells with a composition comprising a nucleic acid non-covalently bound to Insulin-NHCO—CH$_2$—O—N=CH—CO-Lys$_{18}$-Cys(S-Pyridyl)-OH under conditions sufficient to permit internalization and expression of said nucleic acid in said insulin receptor-bearing cells.

5. The method of claim 4, said cells being liver cells.

* * * * *

UNITED STATES PATENT AND TRADEMARK OFFICE
CERTIFICATE OF CORRECTION

PATENT NO.   : 5,830,852
DATED        : November, 3, 1998
INVENTOR(S)  : Thatcher et al.

It is certified that error appears in the above-identified patent and that said Letters Patent is hereby corrected as shown below:

[73]   Assignee:
       Please delete "London" and insert therefor -- Keele --;

Column 1,
Line 64, before Rosenkrantz please insert -- ( --;

Column 2,
Line 25, please delete "H$_2$N-Thr-Lys18-(S-Acetimidomethyl-Cys)-COOH" and insert therefor -- H$_2$N-Thr-Lys$_{18}$-(S-Acetimidomethyl-Cys)-COOH --;

Column 5,
Line 57, please delete "Dornstadt"and insert therefor --Dormstadt --;
Line 62, please delete "MM" and insert therefor -- mM --;

Column 6,
Line 51, please delete "follow" and insert therefor -- following --.

Signed and Sealed this

Thirty-first Day of July, 2001

Attest:

NICHOLAS P. GODICI
Attesting Officer     Acting Director of the United States Patent and Trademark Office

SEQUENCE LISTING ( 1 ) GENERAL INFORMATION:

( i i i ) NUMBER OF SEQUENCES:4

( 2 ) INFORMATION FOR SEQ ID NO: 1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( D ) OTHER INFORMATION: Xaa at position 20 represents
        S- acetimidomethyl-Cys or S-pyridyl-Cys.

( x i ) SEQUENCE DESCRIPTION: SEQ ID NO: 1:

```
Thr  Lys  Lys  Lys  Lys  Lys  Lys  Lys  Lys  Lys  Lys  Lys  Lys  Lys  Lys  Lys
1                  5                          10                         15

Lys  Lys  Lys  Xaa
               20
```

( 2 ) INFORMATION FOR SEQ ID NO: 2:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO: 2:

```
Pro  Lys  Lys  Xaa  Arg  Xaa  Val  Glu  Lys  Lys  Ser  Pro  Lys  Lys  Ala  Lys
1                  5                          10                         15

Lys  Pro  Ala  Lys  Ser  Pro  Ala  Lys  Ala  Lys  Ala  Lys  Ala  Val  Lys  Pro
               20                          25                         30

Lys  Ala  Ala  Lys  Pro  Lys  Lys  Pro  Lys  Lys  Lys  Arg  Lys  Val  Glu  Lys
               35                          40                         45

Lys  Ser  Pro  Lys  Lys  Ala  Lys  Lys  Pro  Ala  Ala  Cys
          50                          55                   60
```

( 2 ) INFORMATION FOR SEQ ID NO: 3:

(i) SEQUENCE CHARACTERISTICS:
    (A) LENGTH: 23 amino acids
    (B) TYPE: amino acid
    (C) STRANDEDNESS: single
    (D) TOPOLOGY: unknown (ii) MOLECULE TYPE: peptide (ix) FEATURE:
    (D) OTHER INFORMATION: Xaa at position 23 represents S-acetimidomethyl-Cys.

(xi) SEQUENCE DESCRIPTION: SEQ ID NO: 3:

Gly Leu Phe Glu Ala Ile Ala Gly Phe Ile Glu Asn Gly Trp Glu Gly
1               5                   10                  15

Met Ile Asp Gly Gly Gly Xaa
            20

(2) INFORMATION FOR SEQ ID NO: 4:

(i) SEQUENCE CHARACTERISTICS:
    (A) LENGTH: 20 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO: 4:

Thr Lys Lys Lys Lys Lys Lys Lys Lys Lys Lys Lys Lys Lys Lys Lys
1               5                   10                  15

Lys Lys Lys Cys
            20